US009579382B2

(12) United States Patent
Triebel

(10) Patent No.: US 9,579,382 B2
(45) Date of Patent: Feb. 28, 2017

(54) USE OF RECOMBINANT LAG-3 OR THE DERIVATIVES THEREOF FOR ELICITING MONOCYTE IMMUNE RESPONSE

(75) Inventor: Frédéric Triebel, Versailles (FR)

(73) Assignee: IMMUTEP, Orsay (FR)

( * ) Notice: Subject to any disclaimer, the term of this patent is extended or adjusted under 35 U.S.C. 154(b) by 276 days.

(21) Appl. No.: 12/681,068

(22) PCT Filed: Oct. 3, 2008

(86) PCT No.: PCT/IB2008/002653
§ 371 (c)(1),
(2), (4) Date: Jul. 20, 2010

(87) PCT Pub. No.: WO2009/044273
PCT Pub. Date: Apr. 9, 2009

(65) Prior Publication Data
US 2011/0008331 A1    Jan. 13, 2011

(30) Foreign Application Priority Data
Oct. 5, 2007   (EP) ..................... 07291214

(51) Int. Cl.
*A61K 38/17* (2006.01)
*A61K 38/19* (2006.01)
*A61K 45/06* (2006.01)
*A61K 31/337* (2006.01)
*A61K 31/704* (2006.01)

(52) U.S. Cl.
CPC ............ *A61K 45/06* (2013.01); *A61K 31/337* (2013.01); *A61K 31/704* (2013.01); *A61K 38/1774* (2013.01)

(58) Field of Classification Search
None
See application file for complete search history.

(56) References Cited

U.S. PATENT DOCUMENTS

| | | | |
|---|---|---|---|
| 5,539,084 A * | 7/1996 | Geysen .................... | 530/334 |
| 5,700,907 A | 12/1997 | Hercend et al. | |
| 5,773,578 A | 6/1998 | Hercend et al. | |
| 5,785,973 A * | 7/1998 | Bixler et al. ............. | 424/196.11 |
| 5,798,231 A | 8/1998 | Hercend et al. | |
| 5,817,511 A | 10/1998 | Hercend et al. | |
| 5,830,758 A | 11/1998 | Hercend et al. | |
| 5,840,839 A * | 11/1998 | Wang et al. .................. | 530/325 |
| 5,874,250 A | 2/1999 | Hercend et al. | |
| 5,955,300 A | 9/1999 | Faure et al. | |
| 5,976,877 A | 11/1999 | Hercend et al. | |
| 6,114,516 A | 9/2000 | Hercend et al. | |
| 6,143,273 A | 11/2000 | Faure et al. | |
| 6,277,368 B1 * | 8/2001 | Hiserodt et al. ........... | 424/93.21 |
| 6,410,509 B1 | 6/2002 | Triebel | |
| 6,482,925 B1 | 11/2002 | El Tayar et al. | |
| 6,596,536 B1 | 7/2003 | Hercend et al. | |
| RE38,313 E | 11/2003 | Faure et al. | |
| 6,855,802 B1 | 2/2005 | Triebel et al. | |
| 6,875,844 B1 | 4/2005 | Ronsin et al. | |
| 7,109,026 B2 | 9/2006 | Triebel | |
| 7,294,712 B2 | 11/2007 | Hercend et al. | |
| 2002/0192195 A1 * | 12/2002 | Triebel ....................... | 424/93.21 |
| 2004/0081686 A1 | 4/2004 | Kravtzoff et al. | |
| 2004/0171551 A1 | 9/2004 | Triebel | |
| 2008/0003235 A1 | 1/2008 | Triebel | |
| 2008/0069770 A1 | 3/2008 | Hercend et al. | |
| 2009/0130054 A1 | 5/2009 | Jooss et al. | |

FOREIGN PATENT DOCUMENTS

| | | |
|---|---|---|
| EP | 0252741 A2 | 1/1988 |
| JP | 2006-124383 A | 5/2006 |
| JP | 2006-141346 A | 6/2006 |
| WO | 96/40210 A1 | 12/1996 |
| WO | WO 98/23741 | 6/1998 |
| WO | WO 98/23748 | 6/1998 |
| WO | 01/35989 A2 | 5/2001 |
| WO | 2005/035779 A2 | 4/2005 |
| WO | WO 2005/103079 A1 | 11/2005 |
| WO | 2009/044273 A2 | 4/2009 |

OTHER PUBLICATIONS

Riott et al., Immunology, Fourth Edition, 1996, Mosby, p. 7.9-7.11.*
Lee et al., J. Immunol., 1999, 163:6292-6300.*
Kirkin et al., 1998, APMIS, 106: 665-679.*
Chaux et al, Int J Cancer, 1998, 77: 538-542.*
Boon, Adv Can Res, 1992, 58:177-210.*
2005 FDA Guidance for Industry Estimating the Maximum Safe Starting Dose in Initial Clinical Trials for Therapeutics in Adult Healthy Volunteers.*
Bukowski et al., J Clin Oncol., 1994, 12:97-106.*
Bock et al., Cancer Res. 1991, 51, 2649-2654.*
Brignone, C. et al.; "IMP321 (sLAG-3) Safety and T Cell Response Potentiation Using an Influenza Vaccine as a Model Antigen: A Single-Blind Phase I Study;" Vaccine, vol. 25, 2007; pp. 4641-4650.
Prigent, Philippe, et al.; "Lymphocyte Activation Gene-3 Induces Tumor Regression and Antitumor Immune Responses;" Eur. J. Immunol., vol. 29, No. 12, Dec. 1, 1999; pp. 3867-3876.
Huard et al. "Characterization of the major histocompatibility complex class II binding site on LAG-3 protein", Proc. Natl. Acad. Sci. USA, vol. 94, pp. 5744-5749, May 1997.
Triebel "LAG-3: a regulator of T-cell and DC responses and its use in therapeutic vaccination", TRENDS in Immunology, vol. 24 No. pp. 619-622, Dec. 2003.
Brignone et al. "A Phase I Pharmacokinetic and Biological Correlative Study of IMP321, a Novel MHC Class II Agonist, in Patients with Advanced Renal Cell Carcinoma", Clin Cancer Res 2009; 15:6225-6231, Sep. 2009.
Brignone et al. "First-line chemoimmunotherapy in metastatic breast carcinoma: combination of paclitaxel and IMP321 (LAG-31g) enhances immune responses and antitumor activity", Journal of Translational Medicine 2010.

(Continued)

*Primary Examiner* — Hong Sang
(74) *Attorney, Agent, or Firm* — Scully Scott Murphy & Presser

(57) ABSTRACT

The present disclosure relates to the use of a recombinant LAG-3 or derivatives thereof in order to boost a monocyte-mediated immune response, in particular to elicit an increase in the number of monocytes in blood. This finds use in the development of novel therapeutic agents for the treatment of an infectious disease or cancer.

9 Claims, 6 Drawing Sheets

(56) References Cited

OTHER PUBLICATIONS

Casati Chiara et al., Soluble Human LAG-3 Molecule Amplifies the in vitro Generation of Type I Tumor-Specific Immunity. Cancer Research; 2006, 66(8): 4450-4460.
Miller et al., Paclitaxel plus bevacizumab versus paclitaxel alone for metastatic breast cancer. The New England Journal of Medicine; 2007, 357(26): 2666-2676.
Principles of cancer therapy. The Merck Manual of Diagnosis and Therapy, 18th Edition, Merck Research Laboratories, 2006, p. 1164, tables 149-152.
Suntharalingam, G. et al., "Cytokine Storm in a Phase 1 Trial of the Anti-CD28 Monoclonal Antibody TGN1412," The New England Journal of Medicine, vol. 355, pp. 1018-1028 (2006).
Brignone, C. et al., "A Soluble Form of Lymphocyte Activation Gene-3 (IMP321) Induces Activation of a Large Range of Human Effector Cytotoxic Cells," The Journal of Immunology vol. 179, pp. 4202-4211 (2007).
Principles of cancer therapy; The Merck Manual of Diagnosis and Therapy, 18th Edition, p. 1164, tables 149-2 (2006).
Fougeray, S. et al., "A soluble LAG-3 protein as an immunopotentiator for therapeutic vaccines: Preclinical evaluation of IMP321", Vaccine, (2006), vol. 24, pp. 5426-5433.

\* cited by examiner

```
SEQUENCE LISTING

<160> NUMBER OF SEQ ID NOS: 17

<210> SEQ ID NO 1
<211> LENGTH: 502
<212> TYPE: PRT
<213> ORGANISM: Homo sapiens
<220> FEATURE:
<221> NAME/KEY: MISC_FEATURE
<222> LOCATION: (1)..(502)
<223> OTHER INFORMATION: hLAG-3 protein

<400> SEQUENCE: 1

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125
```

-continued

```
Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
                180                 185                 190

Glu Ser Pro His His His Leu Ala Glu Ser Phe Leu Phe Leu Pro Gln
            195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
                260                 265                 270

Thr Ala Lys Trp Thr Pro Pro Gly Gly Gly Pro Asp Leu Leu Val Thr
            275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
                340                 345                 350

Ser Gly Gln Glu Arg Phe Val Trp Ser Ser Leu Asp Thr Pro Ser Gln
            355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Leu Phe Leu
                420                 425                 430

Thr Leu Gly Val Leu Ser Leu Leu Leu Leu Val Thr Gly Ala Phe Gly
            435                 440                 445

Phe His Leu Trp Arg Arg Gln Trp Arg Pro Arg Arg Phe Ser Ala Leu
    450                 455                 460

Glu Gln Gly Ile His Pro Gln Ala Gln Ser Lys Ile Glu Glu Leu Glu
465                 470                 475                 480

Gln Glu Pro Glu Pro Glu Pro Glu Pro Glu Pro Glu Pro Glu Pro Glu
                485                 490                 495

Pro Glu Pro Glu Gln Leu
            500
```

<210> SEQ ID NO 2
<211> LENGTH: 426
<212> TYPE: PRT
<213> ORGANISM: Homo sapiens
<220> FEATURE:

<221> NAME/KEY: misc_feature
<222> LOCATION: (1)..(426)
<223> OTHER INFORMATION: Soluble part of hLAG-3 streching from the amino
      acid 23 to 448 of hLAG-3 protein

<400> SEQUENCE: 2

```
Ser Pro Thr Ile Pro Leu Gln Asp Leu Ser Leu Leu Arg Arg Ala Gly
1               5                   10                  15

Val Thr Trp Gln His Gln Pro Asp Ser Gly Pro Pro Ala Ala Ala Pro
            20                  25                  30

Gly His Pro Leu Ala Pro Gly Pro His Pro Ala Ala Pro Ser Ser Trp
        35                  40                  45

Gly Pro Arg Pro Arg Arg Tyr Thr Val Leu Ser Val Gly Pro Gly Gly
    50                  55                  60

Leu Arg Ser Gly Arg Leu Pro Leu Gln Pro Arg Val Gln Leu Asp Glu
65                  70                  75                  80

Arg Gly Arg Gln Arg Gly Asp Phe Ser Leu Trp Leu Arg Pro Ala Arg
                85                  90                  95

Arg Ala Asp Ala Gly Glu Tyr Arg Ala Ala Val His Leu Arg Asp Arg
            100                 105                 110

Ala Leu Ser Cys Arg Leu Arg Leu Arg Leu Gly Gln Ala Ser Met Thr
        115                 120                 125

Ala Ser Pro Pro Gly Ser Leu Arg Ala Ser Asp Trp Val Ile Leu Asn
    130                 135                 140

Cys Ser Phe Ser Arg Pro Asp Arg Pro Ala Ser Val His Trp Phe Arg
145                 150                 155                 160

Asn Arg Gly Gln Gly Arg Val Pro Val Arg Glu Ser Pro His His His
                165                 170                 175

Leu Ala Glu Ser Phe Leu Phe Leu Pro Gln Val Ser Pro Met Asp Ser
            180                 185                 190

Gly Pro Trp Gly Cys Ile Leu Thr Tyr Arg Asp Gly Phe Asn Val Ser
        195                 200                 205

Ile Met Tyr Asn Leu Thr Val Leu Gly Leu Glu Pro Pro Thr Pro Leu
    210                 215                 220

Thr Val Tyr Ala Gly Ala Gly Ser Arg Val Gly Leu Pro Cys Arg Leu
225                 230                 235                 240

Pro Ala Gly Val Gly Thr Arg Ser Phe Leu Thr Ala Lys Trp Thr Pro
                245                 250                 255

Pro Gly Gly Gly Pro Asp Leu Leu Val Thr Gly Asp Asn Gly Asp Phe
            260                 265                 270

Thr Leu Arg Leu Glu Asp Val Ser Gln Ala Gln Ala Gly Thr Tyr Thr
        275                 280                 285

Cys His Ile His Leu Gln Glu Gln Gln Leu Asn Ala Thr Val Thr Leu
    290                 295                 300

Ala Ile Ile Thr Val Thr Pro Lys Ser Phe Gly Ser Pro Gly Ser Leu
305                 310                 315                 320

Gly Lys Leu Leu Cys Glu Val Thr Pro Val Ser Gly Gln Glu Arg Phe
                325                 330                 335

Val Trp Ser Ser Leu Asp Thr Pro Ser Gln Arg Ser Phe Ser Gly Pro
            340                 345                 350

Trp Leu Glu Ala Gln Glu Ala Gln Leu Leu Ser Gln Pro Trp Gln Cys
        355                 360                 365

Gln Leu Tyr Gln Gly Glu Arg Leu Leu Gly Ala Ala Val Tyr Phe Thr
    370                 375                 380
```

-continued

```
Glu Leu Ser Ser Pro Gly Ala Gln Arg Ser Gly Arg Ala Pro Gly Ala
385                 390                 395                 400

Leu Pro Ala Gly His Leu Leu Leu Phe Leu Thr Leu Gly Val Leu Ser
            405                 410                 415

Leu Leu Leu Leu Val Thr Gly Ala Phe Gly
            420                 425

<210> SEQ ID NO 3
<211> LENGTH: 240
<212> TYPE: PRT
<213> ORGANISM: Homo sapiens
<220> FEATURE:
<221> NAME/KEY: misc_feature
<222> LOCATION: (1)..(240)
<223> OTHER INFORMATION: Fragment of hLAG-3 protein consisting of D1 and
      D2

<400> SEQUENCE: 3

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
210                 215                 220

Asp Gly Phe Asn Val Ser Ile Met Tyr Asn Leu Thr Val Leu Gly Leu
225                 230                 235                 240

<210> SEQ ID NO 4
<211> LENGTH: 412
<212> TYPE: PRT
<213> ORGANISM: Homo sapiens
<220> FEATURE:
<221> NAME/KEY: MISC_FEATURE
<222> LOCATION: (1)..(412)
<223> OTHER INFORMATION: Fragment of hLAG-3 protein consisting of D1 to
      D4

<400> SEQUENCE: 4
```

```
Leu Gln Pro Gly Ala Glu Val Pro Val Val Trp Ala Gln Glu Gly Ala
1               5                   10                  15
Pro Ala Gln Leu Pro Cys Ser Pro Thr Ile Pro Leu Gln Asp Leu Ser
            20                  25                  30
Leu Leu Arg Arg Ala Gly Val Thr Trp Gln His Gln Pro Asp Ser Gly
        35                  40                  45
Pro Pro Ala Ala Ala Pro Gly His Pro Leu Ala Pro Gly Pro His Pro
50                      55                  60
Ala Ala Pro Ser Ser Trp Gly Pro Arg Pro Arg Arg Tyr Thr Val Leu
65              70                  75                  80
Ser Val Gly Pro Gly Gly Leu Arg Ser Gly Arg Leu Pro Leu Gln Pro
                85                  90                  95
Arg Val Gln Leu Asp Glu Arg Gly Arg Gln Gly Asp Phe Ser Leu
            100                 105                 110
Trp Leu Arg Pro Ala Arg Arg Ala Asp Ala Gly Glu Tyr Arg Ala Ala
        115                 120                 125
Val His Leu Arg Asp Arg Ala Leu Ser Cys Arg Leu Arg Leu Arg Leu
    130                 135                 140
Gly Gln Ala Ser Met Thr Ala Ser Pro Pro Gly Ser Leu Arg Ala Ser
145                 150                 155                 160
Asp Trp Val Ile Leu Asn Cys Ser Phe Ser Arg Pro Asp Arg Pro Ala
                165                 170                 175
Ser Val His Trp Phe Arg Asn Arg Gly Gln Gly Arg Val Pro Val Arg
            180                 185                 190
Glu Ser Pro His His His Leu Ala Glu Ser Phe Leu Phe Leu Pro Gln
        195                 200                 205
Val Ser Pro Met Asp Ser Gly Pro Trp Gly Cys Ile Leu Thr Tyr Arg
    210                 215                 220
Asp Gly Phe Asn Val Ser Ile Met Tyr Asn Leu Thr Val Leu Gly Leu
225                 230                 235                 240
Glu Pro Pro Thr Pro Leu Thr Val Tyr Ala Gly Ala Gly Ser Arg Val
                245                 250                 255
Gly Leu Pro Cys Arg Leu Pro Ala Gly Val Gly Thr Arg Ser Phe Leu
            260                 265                 270
Thr Ala Lys Trp Thr Pro Pro Gly Gly Gly Pro Asp Leu Leu Val Thr
        275                 280                 285
Gly Asp Asn Gly Asp Phe Thr Leu Arg Leu Glu Asp Val Ser Gln Ala
    290                 295                 300
Gln Ala Gly Thr Tyr Thr Cys His Ile His Leu Gln Glu Gln Gln Leu
305                 310                 315                 320
Asn Ala Thr Val Thr Leu Ala Ile Ile Thr Val Thr Pro Lys Ser Phe
                325                 330                 335
Gly Ser Pro Gly Ser Leu Gly Lys Leu Leu Cys Glu Val Thr Pro Val
            340                 345                 350
Ser Gly Gln Glu Arg Phe Val Trp Ser Ser Leu Asp Thr Pro Ser Gln
        355                 360                 365
Arg Ser Phe Ser Gly Pro Trp Leu Glu Ala Gln Glu Ala Gln Leu Leu
    370                 375                 380
Ser Gln Pro Trp Gln Cys Gln Leu Tyr Gln Gly Glu Arg Leu Leu Gly
385                 390                 395                 400
Ala Ala Val Tyr Phe Thr Glu Leu Ser Ser Pro Gly
                405                 410
```

<210> SEQ ID NO 5
<211> LENGTH: 502
<212> TYPE: PRT
<213> ORGANISM: Homo sapiens
<220> FEATURE:
<221> NAME/KEY: misc_feature
<222> LOCATION: (73)..(73)
<223> OTHER INFORMATION: Mutant R73E of hLAG-3

<400> SEQUENCE: 5

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Glu Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln

```
                355                 360                 365
Arg Ser Phe Ser Gly Pro Trp Leu Glu Ala Gln Glu Ala Gln Leu Leu
370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                    405                 410                 415

Gly Arg Ala Pro Gly Ala Leu Pro Ala Gly His Leu Leu Phe Leu
            420                 425                 430

Thr Leu Gly Val Leu Ser Leu Leu Leu Leu Val Thr Gly Ala Phe Gly
            435                 440                 445

Phe His Leu Trp Arg Arg Gln Trp Arg Pro Arg Arg Phe Ser Ala Leu
450                 455                 460

Glu Gln Gly Ile His Pro Gln Ala Gln Ser Lys Ile Glu Glu Leu Glu
465                 470                 475                 480

Gln Glu Pro Glu Pro Glu Pro Glu Pro Glu Pro Glu Pro Glu Pro Glu
                    485                 490                 495

Pro Glu Pro Glu Gln Leu
            500

<210> SEQ ID NO 6
<211> LENGTH: 502
<212> TYPE: PRT
<213> ORGANISM: Homo sapiens
<220> FEATURE:
<221> NAME/KEY: misc_feature
<222> LOCATION: (75)..(75)
<223> OTHER INFORMATION: Mutant R75X of hLAG-3 X is A or E

<400> SEQUENCE: 6

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
50                  55                  60

Ala Ala Pro Ser Ser Trp Gly Pro Arg Pro Xaa Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
            195                 200                 205
```

```
Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Leu Phe Leu
            420                 425                 430

Thr Leu Gly Val Leu Ser Leu Leu Leu Leu Val Thr Gly Ala Phe Gly
        435                 440                 445

Phe His Leu Trp Arg Arg Gln Trp Arg Pro Arg Arg Phe Ser Ala Leu
450                 455                 460

Glu Gln Gly Ile His Pro Gln Ala Gln Ser Lys Ile Glu Glu Leu Glu
465                 470                 475                 480

Gln Glu Pro Glu Pro Glu Pro Glu Pro Glu Pro Glu Pro Glu Pro Glu
                485                 490                 495

Pro Glu Pro Glu Gln Leu
            500
```

<210> SEQ ID NO 7
<211> LENGTH: 502
<212> TYPE: PRT
<213> ORGANISM: Homo sapiens
<220> FEATURE:
<221> NAME/KEY: MISC_FEATURE
<222> LOCATION: (76)..(76)
<223> OTHER INFORMATION: Mutant R76E of hLAG-3

<400> SEQUENCE: 7

```
Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45
```

```
Pro Pro Ala Ala Ala Pro Gly His Pro Leu Ala Pro Gly Pro His Pro
    50                  55                  60

Ala Ala Pro Ser Ser Trp Gly Pro Arg Pro Arg Glu Tyr Thr Val Leu
 65              70                  75                      80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
        130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
                180                 185                 190

Glu Ser Pro His His His Leu Ala Glu Ser Phe Leu Phe Leu Pro Gln
            195                 200                 205

Val Ser Pro Met Asp Ser Gly Pro Trp Gly Cys Ile Leu Thr Tyr Arg
        210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
                260                 265                 270

Thr Ala Lys Trp Thr Pro Pro Gly Gly Gly Pro Asp Leu Leu Val Thr
            275                 280                 285

Gly Asp Asn Gly Asp Phe Thr Leu Arg Leu Glu Asp Val Ser Gln Ala
        290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
                340                 345                 350

Ser Gly Gln Glu Arg Phe Val Trp Ser Ser Leu Asp Thr Pro Ser Gln
            355                 360                 365

Arg Ser Phe Ser Gly Pro Trp Leu Glu Ala Gln Glu Ala Gln Leu Leu
        370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Leu Phe Leu
            420                 425                 430

Thr Leu Gly Val Leu Ser Leu Leu Leu Val Thr Gly Ala Phe Gly Phe
        435                 440                 445

Phe His Leu Trp Arg Arg Gln Trp Arg Pro Arg Arg Phe Ser Ala Leu
450                 455                 460

Glu Gln Gly Ile His Pro Gln Ala Gln Ser Lys Ile Glu Glu Leu Glu
```

```
             465                 470                 475                 480
Gln Glu Pro Glu Pro Glu Pro Glu Pro Glu Pro Glu
                485                 490                 495
Pro Glu Pro Glu Gln Leu
            500

<210> SEQ ID NO 8
<211> LENGTH: 502
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: Mutant D30A of hLAG-3

<400> SEQUENCE: 8

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Ala Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320
```

-continued

```
Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Leu Phe Leu
            420                 425                 430

Thr Leu Gly Val Leu Ser Leu Leu Leu Leu Val Thr Gly Ala Phe Gly
        435                 440                 445

Phe His Leu Trp Arg Arg Gln Trp Arg Pro Arg Arg Phe Ser Ala Leu
    450                 455                 460

Glu Gln Gly Ile His Pro Gln Ala Gln Ser Lys Ile Glu Glu Leu Glu
465                 470                 475                 480

Gln Glu Pro Glu Pro Glu Pro Glu Pro Glu Pro Glu Pro Glu Pro Glu
                485                 490                 495

Pro Glu Pro Glu Gln Leu
            500

<210> SEQ ID NO 9
<211> LENGTH: 502
<212> TYPE: PRT
<213> ORGANISM: Homo sapiens
<220> FEATURE:
<221> NAME/KEY: MISC_FEATURE
<222> LOCATION: (56)..(56)
<223> OTHER INFORMATION: Mutant H56A of hLAG-3

<400> SEQUENCE: 9

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly Ala Pro Leu Ala Pro Gly His Pro
50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160
```

```
Asp Trp Val Ile Leu Asn Cys Ser Phe Ser Arg Pro Asp Arg Pro Ala
            165                 170                 175

Ser Val His Trp Phe Arg Asn Arg Gly Gln Gly Arg Val Pro Val Arg
        180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
        210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
            245                 250                 255

Gly Leu Pro Cys Arg Leu Pro Ala Gly Val Gly Thr Arg Ser Phe Leu
        260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
        290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
            325                 330                 335

Gly Ser Pro Gly Ser Leu Gly Lys Leu Leu Cys Glu Val Thr Pro Val
        340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
        370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
            405                 410                 415

Gly Arg Ala Pro Gly Ala Leu Pro Ala Gly His Leu Leu Leu Phe Leu
        420                 425                 430

Thr Leu Gly Val Leu Ser Leu Leu Leu Val Thr Gly Ala Phe Gly Phe
        435                 440                 445

Phe His Leu Trp Arg Arg Gln Trp Arg Pro Arg Arg Phe Ser Ala Leu
        450                 455                 460

Glu Gln Gly Ile His Pro Gln Ala Gln Ser Lys Ile Glu Glu Leu Glu
465                 470                 475                 480

Gln Glu Pro Glu Pro Glu Pro Glu Pro Glu Pro Glu Pro Glu Pro Glu
            485                 490                 495

Pro Glu Pro Glu Gln Leu
            500

<210> SEQ ID NO 10
<211> LENGTH: 502
<212> TYPE: PRT
<213> ORGANISM: Homo sapiens
<220> FEATURE:
<221> NAME/KEY: MISC_FEATURE
<222> LOCATION: (77)..(77)
<223> OTHER INFORMATION: Mutant Y77F of hLAG-3

<400> SEQUENCE: 10

Leu Gln Pro Gly Ala Glu Val Pro Val Val Trp Ala Gln Glu Gly Ala
```

-continued

```
  1               5                  10                 15
Pro Ala Gln Leu Pro Cys Ser Pro Thr Ile Pro Leu Gln Asp Leu Ser
                 20                 25                 30

Leu Leu Arg Arg Ala Gly Val Thr Trp Gln His Gln Pro Asp Ser Gly
                 35                 40                 45

Pro Pro Ala Ala Ala Pro Gly His Pro Leu Ala Pro Gly Pro His Pro
 50                      55                 60

Ala Ala Pro Ser Ser Trp Gly Pro Arg Pro Arg Arg Phe Thr Val Leu
 65                 70                 75                      80

Ser Val Gly Pro Gly Gly Leu Arg Ser Gly Arg Leu Pro Leu Gln Pro
                     85                 90                 95

Arg Val Gln Leu Asp Glu Arg Gly Arg Gln Arg Gly Asp Phe Ser Leu
                100                105                110

Trp Leu Arg Pro Ala Arg Arg Ala Asp Ala Gly Glu Tyr Arg Ala Ala
                115                120                125

Val His Leu Arg Asp Arg Ala Leu Ser Cys Arg Leu Arg Leu Arg Leu
            130                135                140

Gly Gln Ala Ser Met Thr Ala Ser Pro Pro Gly Ser Leu Arg Ala Ser
145                     150                155                160

Asp Trp Val Ile Leu Asn Cys Ser Phe Ser Arg Pro Asp Arg Pro Ala
                    165                170                175

Ser Val His Trp Phe Arg Asn Arg Gly Gln Gly Arg Val Pro Val Arg
                180                185                190

Glu Ser Pro His His His Leu Ala Glu Ser Phe Leu Phe Leu Pro Gln
                195                200                205

Val Ser Pro Met Asp Ser Gly Pro Trp Gly Cys Ile Leu Thr Tyr Arg
210                 215                    220

Asp Gly Phe Asn Val Ser Ile Met Tyr Asn Leu Thr Val Leu Gly Leu
225                 230                    235                240

Glu Pro Pro Thr Pro Leu Thr Val Tyr Ala Gly Ala Gly Ser Arg Val
                245                250                255

Gly Leu Pro Cys Arg Leu Pro Ala Gly Val Gly Thr Arg Ser Phe Leu
                260                265                270

Thr Ala Lys Trp Thr Pro Pro Gly Gly Gly Pro Asp Leu Leu Val Thr
            275                280                285

Gly Asp Asn Gly Asp Phe Thr Leu Arg Leu Glu Asp Val Ser Gln Ala
            290                295                300

Gln Ala Gly Thr Tyr Thr Cys His Ile His Leu Gln Glu Gln Gln Leu
305                 310                    315                320

Asn Ala Thr Val Thr Leu Ala Ile Ile Thr Val Thr Pro Lys Ser Phe
                    325                330                335

Gly Ser Pro Gly Ser Leu Gly Lys Leu Leu Cys Glu Val Thr Pro Val
                340                345                350

Ser Gly Gln Glu Arg Phe Val Trp Ser Ser Leu Asp Thr Pro Ser Gln
                355                360                365

Arg Ser Phe Ser Gly Pro Trp Leu Glu Ala Gln Glu Ala Gln Leu Leu
            370                375                380

Ser Gln Pro Trp Gln Cys Gln Leu Tyr Gln Gly Glu Arg Leu Leu Gly
385                 390                    395                400

Ala Ala Val Tyr Phe Thr Glu Leu Ser Ser Pro Gly Ala Gln Arg Ser
                    405                410                415

Gly Arg Ala Pro Gly Ala Leu Pro Ala Gly His Leu Leu Leu Phe Leu
            420                425                430
```

```
Thr Leu Gly Val Leu Ser Leu Leu Leu Val Thr Gly Ala Phe Gly
            435                 440                 445

Phe His Leu Trp Arg Arg Gln Trp Arg Pro Arg Arg Phe Ser Ala Leu
450                 455                 460

Glu Gln Gly Ile His Pro Gln Ala Gln Ser Lys Ile Glu Gln Leu Glu
465                 470                 475                 480

Gln Glu Pro Glu Pro Glu Pro Glu Pro Glu Pro Glu Pro Glu Pro Glu
                485                 490                 495

Pro Glu Pro Glu Gln Leu
            500

<210> SEQ ID NO 11
<211> LENGTH: 502
<212> TYPE: PRT
<213> ORGANISM: Homo sapiens
<220> FEATURE:
<221> NAME/KEY: MISC_FEATURE
<222> LOCATION: (88)..(88)
<223> OTHER INFORMATION: Mutant R88A of hLAG-3

<400> SEQUENCE: 11

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Ala Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270
```

-continued

```
Thr Ala Lys Trp Thr Pro Pro Gly Gly Pro Asp Leu Val Thr
            275                 280                 285
Gly Asp Asn Gly Asp Phe Thr Leu Arg Leu Glu Asp Val Ser Gln Ala
290                 295                 300
Gln Ala Gly Thr Tyr Thr Cys His Ile His Leu Gln Glu Gln Gln Leu
305                 310                 315                 320
Asn Ala Thr Val Thr Leu Ala Ile Ile Thr Val Thr Pro Lys Ser Phe
                325                 330                 335
Gly Ser Pro Gly Ser Leu Gly Lys Leu Leu Cys Glu Val Thr Pro Val
            340                 345                 350
Ser Gly Gln Glu Arg Phe Val Trp Ser Ser Leu Asp Thr Pro Ser Gln
            355                 360                 365
Arg Ser Phe Ser Gly Pro Trp Leu Glu Ala Gln Glu Ala Gln Leu Leu
370                 375                 380
Ser Gln Pro Trp Gln Cys Gln Leu Tyr Gln Gly Glu Arg Leu Leu Gly
385                 390                 395                 400
Ala Ala Val Tyr Phe Thr Glu Leu Ser Ser Pro Gly Ala Gln Arg Ser
                405                 410                 415
Gly Arg Ala Pro Gly Ala Leu Pro Ala Gly His Leu Leu Phe Leu
            420                 425                 430
Thr Leu Gly Val Leu Ser Leu Leu Leu Leu Val Thr Gly Ala Phe Gly
            435                 440                 445
Phe His Leu Trp Arg Arg Gln Trp Arg Pro Arg Arg Phe Ser Ala Leu
450                 455                 460
Glu Gln Gly Ile His Pro Gln Ala Gln Ser Lys Ile Glu Glu Leu Glu
465                 470                 475                 480
Gln Glu Pro Glu Pro Glu Pro Glu Pro Glu Pro Glu Pro Glu Pro Glu
                485                 490                 495
Pro Glu Pro Glu Gln Leu
            500

<210> SEQ ID NO 12
<211> LENGTH: 502
<212> TYPE: PRT
<213> ORGANISM: Homo sapiens
<220> FEATURE:
<221> NAME/KEY: MISC_FEATURE
<222> LOCATION: (103)..(103)
<223> OTHER INFORMATION: Mutant R103A of hLAG-3

<400> SEQUENCE: 12

Leu Gln Pro Gly Ala Glu Val Pro Val Val Trp Ala Gln Glu Gly Ala
1               5                   10                  15
Pro Ala Gln Leu Pro Cys Ser Pro Thr Ile Pro Leu Gln Asp Leu Ser
                20                  25                  30
Leu Leu Arg Arg Ala Gly Val Thr Trp Gln His Gln Pro Asp Ser Gly
            35                  40                  45
Pro Pro Ala Ala Ala Pro Gly His Pro Leu Ala Pro Gly Pro His Pro
        50                  55                  60
Ala Ala Pro Ser Ser Trp Gly Pro Arg Pro Arg Arg Tyr Thr Val Leu
65                  70                  75                  80
Ser Val Gly Pro Gly Gly Leu Arg Ser Gly Arg Leu Pro Leu Gln Pro
                85                  90                  95
Arg Val Gln Leu Asp Glu Ala Gly Arg Gln Arg Gly Asp Phe Ser Leu
                100                 105                 110
Trp Leu Arg Pro Ala Arg Arg Ala Asp Ala Gly Glu Tyr Arg Ala Ala
```

```
            115                 120                 125
Val His Leu Arg Asp Arg Ala Leu Ser Cys Arg Leu Arg Leu
130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Pro Asp Leu Leu Val Thr
        275                 280                 285

Gly Asp Asn Gly Asp Phe Thr Leu Arg Leu Glu Asp Val Ser Gln Ala
290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Phe Leu
            420                 425                 430

Thr Leu Gly Val Leu Ser Leu Leu Leu Leu Val Thr Gly Ala Phe Gly
        435                 440                 445

Phe His Leu Trp Arg Arg Gln Trp Arg Pro Arg Arg Phe Ser Ala Leu
450                 455                 460

Glu Gln Gly Ile His Pro Gln Ala Gln Ser Lys Ile Glu Glu Leu Glu
465                 470                 475                 480

Gln Glu Pro Glu Pro Glu Pro Glu Pro Glu Pro Glu Pro Glu Pro Glu
                485                 490                 495

Pro Glu Pro Glu Gln Leu
            500

<210> SEQ ID NO 13
<211> LENGTH: 502
<212> TYPE: PRT
<213> ORGANISM: Homo sapiens
```

-continued

```
<220> FEATURE:
<221> NAME/KEY: MISC_FEATURE
<222> LOCATION: (109)..(109)
<223> OTHER INFORMATION: Mutant D109E of hLAG-3

<400> SEQUENCE: 13

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Glu Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Pro Asp Leu Leu Val Thr
        275                 280                 285

Gly Asp Asn Gly Asp Phe Thr Leu Arg Leu Glu Asp Val Ser Gln Ala
    290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
    370                 375                 380
```

```
Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
            405                 410                 415

Gly Arg Ala Pro Gly Ala Leu Pro Ala Gly His Leu Leu Phe Leu
                420                 425                 430

Thr Leu Gly Val Leu Ser Leu Leu Leu Val Thr Gly Ala Phe Gly
        435                 440                 445

Phe His Leu Trp Arg Arg Gln Trp Arg Pro Arg Arg Phe Ser Ala Leu
        450                 455                 460

Glu Gln Gly Ile His Pro Gln Ala Gln Ser Lys Ile Glu Glu Leu Glu
465                 470                 475                 480

Gln Glu Pro Glu Pro Glu Pro Glu Pro Glu Pro Glu Pro Glu Pro Glu
            485                 490                 495

Pro Glu Pro Glu Gln Leu
                500

<210> SEQ ID NO 14
<211> LENGTH: 502
<212> TYPE: PRT
<213> ORGANISM: Homo sapiens
<220> FEATURE:
<221> NAME/KEY: MISC_FEATURE
<222> LOCATION: (115)..(115)
<223> OTHER INFORMATION: Mutant R115A of hLAG-3

<400> SEQUENCE: 14

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Ala Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
    130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
    210                 215                 220

Asp Gly Phe Asn Val Ser Ile Met Tyr Asn Leu Thr Val Leu Gly Leu
```

```
                225                 230                 235                 240
    Glu Pro Pro Thr Pro Leu Thr Val Tyr Ala Gly Ala Gly Ser Arg Val
                        245                 250                 255

Gly Leu Pro Cys Arg Leu Pro Ala Gly Val Gly Thr Arg Ser Phe Leu
                        260                 265                 270

Thr Ala Lys Trp Thr Pro Pro Gly Gly Pro Asp Leu Leu Val Thr
                        275                 280                 285

Gly Asp Asn Gly Asp Phe Thr Leu Arg Leu Glu Asp Val Ser Gln Ala
                290                 295                 300

Gln Ala Gly Thr Tyr Thr Cys His Ile His Leu Gln Glu Gln Gln Leu
    305                 310                 315                 320

Asn Ala Thr Val Thr Leu Ala Ile Ile Thr Val Thr Pro Lys Ser Phe
                        325                 330                 335

Gly Ser Pro Gly Ser Leu Gly Lys Leu Leu Cys Glu Val Thr Pro Val
                        340                 345                 350

Ser Gly Gln Glu Arg Phe Val Trp Ser Ser Leu Asp Thr Pro Ser Gln
                        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
    385                 390                 395                 400

Ala Ala Val Tyr Phe Thr Glu Leu Ser Ser Pro Gly Ala Gln Arg Ser
                        405                 410                 415

Gly Arg Ala Pro Gly Ala Leu Pro Ala Gly His Leu Leu Leu Phe Leu
                        420                 425                 430

Thr Leu Gly Val Leu Ser Leu Leu Leu Val Thr Gly Ala Phe Gly
                        435                 440                 445

Phe His Leu Trp Arg Arg Gln Trp Arg Pro Arg Arg Phe Ser Ala Leu
                        450                 455                 460

Glu Gln Gly Ile His Pro Gln Ala Gln Ser Lys Ile Glu Gln Leu Glu
    465                 470                 475                 480

Gln Glu Pro Glu Pro Glu Pro Glu Pro Glu Pro Glu Pro Glu Pro Glu
                        485                 490                 495

Pro Glu Pro Glu Gln Leu
                    500

<210> SEQ ID NO 15
<211> LENGTH: 492
<212> TYPE: PRT
<213> ORGANISM: Homo sapiens
<220> FEATURE:
<221> NAME/KEY: MISC_FEATURE
<222> LOCATION: (54)..(55)
<223> OTHER INFORMATION: Deletion of 11 amino acids 55"GHPLAPGPHPA"65
      of hLAG-3

<400> SEQUENCE: 15

Leu Gln Pro Gly Ala Glu Val Pro Val Val Trp Ala Gln Glu Gly Ala
    1                   5                   10                  15

Pro Ala Gln Leu Pro Cys Ser Pro Thr Ile Pro Leu Gln Asp Leu Ser
                        20                  25                  30

Leu Leu Arg Arg Ala Gly Val Thr Trp Gln His Gln Pro Asp Ser Gly
                        35                  40                  45

Pro Pro Ala Ala Ala Pro Gly Ala Pro Ser Ser Trp Gly Pro Arg Pro
                        50                  55                  60

Arg Arg Tyr Thr Val Leu Ser Val Gly Pro Gly Gly Leu Arg Ser Gly
```

-continued

```
                65                  70                  75                  80
Arg Leu Pro Leu Gln Pro Arg Val Gln Leu Asp Glu Arg Gly Arg Gln
                    85                  90                  95
Arg Gly Asp Phe Ser Leu Trp Leu Arg Pro Ala Arg Arg Ala Asp Ala
                100                 105                 110
Gly Glu Tyr Arg Ala Ala Val His Leu Arg Asp Arg Ala Leu Ser Cys
                115                 120                 125
Arg Leu Arg Leu Arg Leu Gly Gln Ala Ser Met Thr Ala Ser Pro Pro
                130                 135                 140
Gly Ser Leu Arg Ala Ser Asp Trp Val Ile Leu Asn Cys Ser Phe Ser
145                 150                 155                 160
Arg Pro Asp Arg Pro Ala Ser Val His Trp Phe Arg Asn Arg Gly Gln
                165                 170                 175
Gly Arg Val Pro Val Arg Glu Ser Pro His His Leu Ala Glu Ser
                180                 185                 190
Phe Leu Phe Leu Pro Gln Val Ser Pro Met Asp Ser Gly Pro Trp Gly
                195                 200                 205
Cys Ile Leu Thr Tyr Arg Asp Gly Phe Asn Val Ser Ile Met Tyr Asn
                210                 215                 220
Leu Thr Val Leu Gly Leu Glu Pro Pro Thr Pro Leu Thr Val Tyr Ala
225                 230                 235                 240
Gly Ala Gly Ser Arg Val Gly Leu Pro Cys Arg Leu Pro Ala Gly Val
                245                 250                 255
Gly Thr Arg Ser Phe Leu Thr Ala Lys Trp Thr Pro Pro Gly Gly Gly
                260                 265                 270
Pro Asp Leu Leu Val Thr Gly Asp Asn Gly Asp Phe Thr Leu Arg Leu
                275                 280                 285
Glu Asp Val Ser Gln Ala Gln Ala Gly Thr Tyr Thr Cys His Ile His
                290                 295                 300
Leu Gln Glu Gln Gln Leu Asn Ala Thr Val Thr Leu Ala Ile Ile Thr
305                 310                 315                 320
Val Thr Pro Lys Ser Phe Gly Ser Pro Gly Ser Leu Gly Lys Leu Leu
                325                 330                 335
Cys Glu Val Thr Pro Val Ser Gly Gln Glu Arg Phe Val Trp Ser Ser
                340                 345                 350
Leu Asp Thr Pro Ser Gln Arg Ser Phe Ser Gly Pro Trp Leu Glu Ala
                355                 360                 365
Gln Glu Ala Gln Leu Leu Ser Gln Pro Trp Gln Cys Gln Leu Tyr Gln
                370                 375                 380
Gly Glu Arg Leu Leu Gly Ala Ala Val Tyr Phe Thr Glu Leu Ser Ser
385                 390                 395                 400
Pro Gly Ala Gln Arg Ser Gly Arg Ala Pro Gly Ala Leu Pro Ala Gly
                405                 410                 415
His Leu Leu Leu Phe Leu Thr Leu Gly Val Leu Ser Leu Leu Leu Leu
                420                 425                 430
Val Thr Gly Ala Phe Gly Phe His Leu Trp Arg Arg Gln Trp Arg Pro
                435                 440                 445
Arg Arg Phe Ser Ala Leu Glu Gln Gly Ile His Pro Gln Ala Gln Ser
                450                 455                 460
Lys Ile Glu Glu Leu Glu Gln Glu Pro Glu Pro Glu Pro Glu Pro Glu
465                 470                 475                 480
Pro Glu Pro Glu Pro Glu Pro Glu Gln Leu
                485                 490
```

```
<210> SEQ ID NO 16
<211> LENGTH: 330
<212> TYPE: PRT
<213> ORGANISM: Homo sapiens
<220> FEATURE:
<221> NAME/KEY: MISC_FEATURE
<222> LOCATION: (1)..(330)
<223> OTHER INFORMATION: Fragment of hLAG-3 protein consisting of
      D1, D2 and D3

<400> SEQUENCE: 16

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
            20                  25                  30

Leu Leu Arg Arg Ala Gly Val Thr Trp Gln His Gln Pro Asp Ser Gly
        35                  40                  45

Pro Pro Ala Ala Ala Pro Gly His Pro Leu Ala Pro Gly Pro His Pro
    50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
            100                 105                 110

Trp Leu Arg Pro Ala Arg Arg Ala Asp Ala Gly Glu Tyr Arg Ala Ala
        115                 120                 125

Val His Leu Arg Asp Arg Ala Leu Ser Cys Arg Leu Arg Leu Arg Leu
130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
            180                 185                 190

Glu Ser Pro His His Leu Ala Glu Ser Phe Leu Phe Leu Pro Gln
        195                 200                 205

Val Ser Pro Met Asp Ser Gly Pro Trp Gly Cys Ile Leu Thr Tyr Arg
210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
            260                 265                 270

Thr Ala Lys Trp Thr Pro Pro Gly Gly Gly Pro Asp Leu Leu Val Thr
        275                 280                 285

Gly Asp Asn Gly Asp Phe Thr Leu Arg Leu Glu Asp Val Ser Gln Ala
290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr
                325                 330

<210> SEQ ID NO 17
```

```
<211> LENGTH: 654
<212> TYPE: PRT
<213> ORGANISM: Homo sapiens
<220> FEATURE:
<221> NAME/KEY: MISC_FEATURE
<222> LOCATION: (1)..(654)
<223> OTHER INFORMATION: Recombinant soluble human LAG-3Ig fusion
      protein (IMP321)
<220> FEATURE:
<221> NAME/KEY: MISC_FEATURE
<222> LOCATION: (413)..(422)
<223> OTHER INFORMATION: Linker peptide between the hLAG-3 D4 domain
      and the hinge region of a hinge-CH2-CH3 hIgG1 Fc region

<400> SEQUENCE: 17
```

Leu Gln Pro Gly Ala Glu Val Pro Val Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
        50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
        130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
                180                 185                 190

Glu Ser Pro His His His Leu Ala Glu Ser Phe Leu Phe Leu Pro Gln
            195                 200                 205

Val Ser Pro Met Asp Ser Gly Pro Trp Gly Cys Ile Leu Thr Tyr Arg
210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
                260                 265                 270

Thr Ala Lys Trp Thr Pro Pro Gly Gly Gly Pro Asp Leu Leu Val Thr
            275                 280                 285

Gly Asp Asn Gly Asp Phe Thr Leu Arg Leu Glu Asp Val Ser Gln Ala
        290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

```
Gly Ser Pro Gly Ser Leu Gly Lys Leu Leu Cys Glu Val Thr Pro Val
            340                 345                 350

Ser Gly Gln Glu Arg Phe Val Trp Ser Ser Leu Asp Thr Pro Ser Gln
        355                 360                 365

Arg Ser Phe Ser Gly Pro Trp Leu Glu Ala Gln Glu Ala Gln Leu Leu
    370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Asp Asp Asp Asp
                405                 410                 415

Lys Gly Ser Gly Ser Gly Glu Pro Lys Ser Cys Asp Lys Thr His Thr
            420                 425                 430

Cys Pro Pro Cys Pro Ala Pro Glu Leu Leu Gly Gly Pro Ser Val Phe
            435                 440                 445

Leu Phe Pro Pro Lys Pro Lys Asp Thr Leu Met Ile Ser Arg Thr Pro
    450                 455                 460

Glu Val Thr Cys Val Val Val Asp Val Ser His Glu Asp Pro Glu Val
465                 470                 475                 480

Lys Phe Asn Trp Tyr Val Asp Gly Val Glu Val His Asn Ala Lys Thr
            485                 490                 495

Lys Pro Arg Glu Glu Gln Tyr Asn Ser Thr Tyr Arg Val Val Ser Val
            500                 505                 510

Leu Thr Val Leu His Gln Asp Trp Leu Asn Gly Lys Glu Tyr Lys Cys
        515                 520                 525

Lys Val Ser Asn Lys Ala Leu Pro Ala Pro Ile Glu Lys Thr Ile Ser
    530                 535                 540

Lys Ala Lys Gly Gln Pro Arg Glu Pro Gln Val Tyr Thr Leu Pro Pro
545                 550                 555                 560

Ser Arg Asp Glu Leu Thr Lys Asn Gln Val Ser Leu Thr Cys Leu Val
            565                 570                 575

Lys Gly Phe Tyr Pro Ser Asp Ile Ala Val Glu Trp Glu Ser Asn Gly
            580                 585                 590

Gln Pro Glu Asn Asn Tyr Lys Thr Thr Pro Pro Val Leu Asp Ser Asp
        595                 600                 605

Gly Ser Phe Phe Leu Tyr Ser Lys Leu Thr Val Asp Lys Ser Arg Trp
    610                 615                 620

Gln Gln Gly Asn Val Phe Ser Cys Ser Val Met His Glu Ala Leu His
625                 630                 635                 640

Asn His Tyr Thr Gln Lys Ser Leu Ser Leu Ser Pro Gly Lys
            645                 650
```

USE OF RECOMBINANT LAG-3 OR THE DERIVATIVES THEREOF FOR ELICITING MONOCYTE IMMUNE RESPONSE

CROSS-REFERENCE TO RELATED APPLICATIONS

This application is a National Phase Entry of International Application No. PCT/IB2008/002653, filed on Oct. 3, 2008, which claims priority to European Application EP 07291214.0, filed on Oct. 5, 2007, both of which are incorporated by reference herein.

BACKGROUND

Technical Field

The present invention relates to the use of recombinant LAG-3 or derivatives thereof in order to boost a monocyte-mediated immune response. It enables an increase in monocyte numbers in blood. It finds many applications in particular in the development of novel therapeutic agents in cancer immunotherapy.

State of the Art

In the description which follows, the references between brackets [ ] refer to the attached reference list. The lymphocyte activation gene 3 (hlag-3) expressed in human $CD4^+$ and $CD8^+$ activated T cells as well as in activated NK cells encodes a 503 amino acids type I membrane protein (LAG-3) with four extracellular immunoglobulin superfamily (IgSF) domains [1]. A murine lymphocyte activation gene 3 (mlag-3) was cloned and approximatively 70% of homology was found with hlag-3, with the same proline rich motif in the intracytoplasmic tail.

LAG-3 (CD223), described as being a natural high affinity ligand for MHC class II, is known to induce maturation of monocyte-derived dendritic cells in vitro, and is used as an immunotherapy adjuvant to induce CD4 T helper type 1 responses and CD8 T cell responses in vivo [2]. Further information regarding LAG-3 and its use as an immunostimulant may be found in TRIEBEL et al. [1], TRIEBEL et al. [3], and HUARD et al. [4]. Some forms of soluble LAG-3 can bind to MHC class II molecules and can induce dendritic cells to mature and migrate to secondary lymphoid organs where they can prime naïve CD4-helper and CD8-cytotoxic T cells leading to tumour rejection [5]. More recently a recombinant soluble human LAG-3Ig fusion protein (IMP321) was shown to activate a large range of effector cells in both innate and acquired immune responses, for example inducing monocytes-macrophages to secrete cytokines/chemokines [6].

Monocytes are produced by the bone marrow from haematopoietic stem cell precursors called monoblasts. They constitute between three to eight percent of the leukocytes in the blood. Monocytes circulate in the bloodstream for about 24 hours (half-life of 8 hours) and then typically move into tissues throughout the body. In the tissues, monocytes mature into macrophages, epitheloid cells or antigen-presenting cells (APCs, for example dendritic cells). Monocytes are responsible for phagocytosis (ingestion) of foreign substances in the body. Monocytes can perform phagocytosis using intermediary (opsonising) proteins such as antibodies or complement that coat the pathogen, as well as by binding to the pathogen directly via pattern-recognition receptors that recognize pathogens. Monocytes are also capable of killing infected host cells via antibody, termed antibody-dependent cell-mediated cytotoxicity (ADCC). Due to their secretion and phagocytosis properties, monocytes-macrophages occur in aspecific and specific immune response.

The study of membrane markers allows the identification of monocyte populations, mature or not, dystrophic or not. The molecules present on monocyte membranes, mature or not, are almost always non specific but correspond to the following activities:

receptor for the Fc fragment of IgG (CD16, CD32, CD64),
receptor for the Fc fragment of IgE (CD23),
receptor for complement fractions (CD11b, CD21/CD35),
leukocyte adhesion proteins (CD11a, CD11c),
protein facilitating binding to LPS of Gram-bacteria (CD14),
protein with tyrosine phosphatase activity (CD45).

SUMMARY

The authors of the present invention have now discovered, entirely unexpectedly, that human LAG-3 or derivatives thereof when inoculated into patients with highly malignant tumors, for example patients with metastatic breast cancer (MBC) or metastatic renal clear-cell carcinoma (MRCC), induced a potent immunity which is monocyte dependent. Said induced immunity manifests itself by a significant increase in blood monocyte counts.

This result was achieved by means of plural administration of LAG-3 or derivatives thereof to patients receiving immunotherapy or chemo-immunotherapy. This result is rather surprising since binding to, and activation of, monocytes is not expected to be followed by monocyte expansion. Indeed monocytes are end-of-differentiation hematopoietic cells and can not proliferate. They can stay in the blood as monocytes or differentiate toward either macrophages or dendritic cells under the influence of different cytokines, until they die. Thus it is believed, without limitation to the following theory, that the mechanism of action involved may be a proliferative signal directed to hematopoietic precursor cells (before the promonocyte stage) residing in the bone marrow, or an increase in the half-life or residence time of mature circulating monocytes.

Therefore the present invention relates to the use of a recombinant LAG-3 protein or derivative thereof that elicits monocyte mediated immune response, for the manufacture of a medicament inducing an increase in monocyte numbers for the treatment of an infectious disease or cancer. By "derivatives of LAG-3", in the sense of the present invention, is meant mutants, variants and fragments of LAG-3 provided that they maintain the ability of LAG-3 to bind MHC class II molecules.

Thus, the following forms of LAG-3 may be used:
the whole LAG-3 protein,
a soluble polypeptide fragment thereof consisting of at least one of the four immunoglobulin extracellular domains, namely the soluble part of LAG-3 comprised of the extracellular region stretching from the amino acid 23 to the amino acid 448 o the LAG-3 sequence disclosed in French patent Application FR 90 00 126,
a fragment of LAG-3 consisting of substantially all of the first and second domains,
a fragment of LAG-3 consisting of substantially all of the first and second domains or all of the four domains, such as defined in WO 95/30750,
a mutant form of soluble LAG-3 or a fragment thereof comprising the D1 and D2 extracellular domains and consisting of:

a substitution of an amino acid at one of the following positions:
position 73 where ARG is substituted with GLU,
position 75 where ARG is substituted with ALA or GLU,
position 76 where ARG is substituted with GLU,
or a combination of two or more of those substitutions,
a substitution of an amino acid at one of the following positions:
position 30 where ASP is substituted with ALA,
position 56 where HIS is substituted with ALA,
position 77 where TYR is substituted with PHE,
position 88 where ARG is substituted with ALA,
position 103 where ARG is substituted with ALA,
position 109 where ASP is substituted with GLU,
position 115 where ARG is substituted with ALA,
or a deletion of the region comprised between the position 54 and the position 66,
or a combination of two or more of those substitutions.

Those mutants are described by HUARD et al. (Proc. Natl. Acad. Sci. USA, 11: 5744-5749, 1997).

a physiological variant of LAG-3 comprised of the soluble 52 kDa protein containing D1, D2 and D3.

a recombinant soluble human LAG-3Ig fusion protein (IMP321), a 200-kDa dimer produced in Chinese hamster ovary cells transfected with a plasmid encoding for the extracellular domain of hLAG-3 fused to the human IgG1 Fc.

By "medicament", in the sense of the present invention, is meant an effective plurality of doses of a recombinant LAG-3 protein or derivative thereof. By "effective plurality of doses of a recombinant LAG-3 protein or derivative thereof", in the sense of the present invention, is meant a formulation that allows administration of one dose of a recombinant LAG-3 protein or derivative thereof every one to several weeks for at least 12 weeks, and preferably for at least 24 weeks, separated by 13-day±2 days administration-free intervals. Advantageously, the administration is an every-two-week schedule. By "one dose of a recombinant LAG-3 protein or derivative thereof", in the sense of the present invention, is meant a formulation that allows one administration in the range of 0.25-30 mg, preferably 1-6.25 mg, more preferably 6-30 mg, and for example about 1.25 mg of recombinant LAG-3 protein or derivative thereof to a patient in need thereof having a body mass index (weight/height$^2$) in the range of 18-30 kg/m$^2$.

The recombinant LAG-3 or derivatives thereof are administered in a free form, for example in a soluble form by inoculating them systemically, for example as a subcutaneous, intramuscular or intravenous injection, preferably as a subcutaneous injection. Said recombinant LAG-3 or derivatives thereof may also be formulated so as to allow administration with a compound having anti-cancer or anti-infectious disease immunotherapeutical or chemotherapeutical properties. By "administration with a compound", in the sense of the present invention, is meant an administration of a recombinant LAG-3 or derivative thereof before, with, or subsequent to, the administration of said compound. By "compound having anti-cancer or anti-infectious disease chemotherapeutical properties", in the sense of the present invention, is meant for example a chemotherapy agent selected from the group consisting of taxanes (paclitaxel, docetaxel), gemcitabine and anthracyclines (doxorubicine) or an anti-viral agent such as ribavirin.

In a particular embodiment of the invention, recombinant LAG-3 protein or derivative thereof is administered to patients after the first administration of the cytotoxic compound having anti-cancer or anti-infectious disease chemotherapeutical properties. Advantageously, recombinant LAG-3 protein or derivative thereof is administered to patients is administered 12 to 96 hours after the administration of the cytotoxic compound having anti-cancer or anti-infectious disease chemotherapeutical properties. In another embodiment, recombinant LAG-3 protein or derivative thereof is administered to patients is administered one or two days after the first administration of the compound having anti-cancer or anti-infectious disease chemotherapeutical properties. In another particular embodiment of the invention, recombinant LAG-3 protein or derivative and the cytotoxic compound having anti-cancer or anti-infectious disease chemotherapeutical properties are administered simultaneously, separately or sequentially.

Advantageously, in this particular embodiment of the invention, recombinant LAG-3 protein or derivative thereof is administered at least six times, for example seven times, ten times, twelve times or more. Advantageously, in this particular embodiment of the invention, recombinant LAG-3 protein or derivative thereof is administered on an every-two-week schedule. Advantageously, recombinant LAG-3 protein or derivative thereof is administered at a dose comprised between 0.25 to 30 mg, eventually at a dose comprised between 6 to 30 mg, eventually at a dose comprised between 8 to 25 mg, eventually between 12 and 20 mg. By "compound having anti-cancer or anti-infectious disease immunotherapeutical properties", in the sense of the present invention, is also meant for example a compound selected from the group consisting of therapeutic antibodies killing tumour cells through ADCC (antibody-dependent cell cytotoxicity), and mixtures thereof, and preferably from the group consisting of rituximab, cetuximab, edrecolomab, and trastuzumab.

In a particular embodiment of the invention, recombinant LAG-3 protein or derivative thereof and therapeutic antibodies are administered to patients simultaneously, separately or sequentially. Advantageously, in a particular embodiment of the invention, recombinant LAG-3 protein or derivative thereof is administered to patients the same day as therapeutic antibodies.

The present invention also relates to kit-of-parts, i.e. a combined preparation, containing recombinant LAG-3 protein or derivative thereof and a therapeutic antibody for simultaneous, separate or sequential use. Advantageously, the kit-of-parts contains recombinant LAG-3 protein or derivative thereof and a therapeutic antibody selected from the group consisting of rituximab, cetuximab, edrecolomab, and trastuzumab. Preferentially, the kit-of-part of the invention contain recombinant LAG-3 protein or derivative thereof and rituximab.

In the kit-of-parts of the invention, recombinant LAG-3 protein or derivative thereof and a therapeutic antibody form a functional unity, because of a synergistic cytotoxic effect between the two components. This effect is a new joint effect, because the two components administered alone does not have the same effect as when administered as a combined preparation. The present invention also relates to kit-of-parts, i.e. a combined preparation, containing recombinant LAG-3 protein or derivative thereof and a compound having anti-cancer or anti-infectious disease chemotherapeutical properties for simultaneous, separate or sequential use. Advantageously, the kit-of-parts contains recombinant LAG-3 protein or derivative thereof and a compound having anti-cancer or anti-infectious disease chemotherapeutical properties selected from the group consisting of taxanes (paclitaxel, docetaxel), gemcitabine and anthracyclines (doxorubicine).

The present invention also relates to a method for treating a pathological condition involving a monocyte mediated immune response, comprising administering the medicament as above defined to a patient in need thereof. By "pathological condition involving a monocyte mediated immune response", in the sense of the present invention, is meant viral infectious diseases, parasitic infectious diseases, bacterial infectious diseases, and cancer. Other advantages may also appear to one skilled in the art from the non-limitative examples given below, and illustrated by the enclosed figures.

DETAILED DESCRIPTION

Example 1

Monocytes Increase in Metastatic Breast Cancer (MBC) Patients Using Low IMP321 Dose Five MBC patients, receiving chemotherapy known to induce tumour cell apoptosis, each received one subcutaneous IMP321 dose of 0.25 mg 1-2 days after chemotherapy every other week, for 24 weeks, separated by 14-day administration-free intervals. Blood samples were collected in heparinated lithium tubes (Vacutainer; BD Biosciences) from each patient, 14 days after the last IMP321 injection (i.e. looking at lasting immunomodulatory effects of the product), at 3 months (Day 85) and 6 months (Day 170). PBMCs were isolated on Ficoll-Paque gradient (Pharmacia) using LeucoSep tubes (Greiner Bio-One), and used immediately. The increase in number of monocytes was analysed by fluorescence-activated cell sorting (FACS) in said fresh PBMC samples (because monocytes are sensitive to freezing), and compared with the monocyte counts carried out on fresh PBMC samples collected before IMP321 administration (Day 1).

Figure 1:
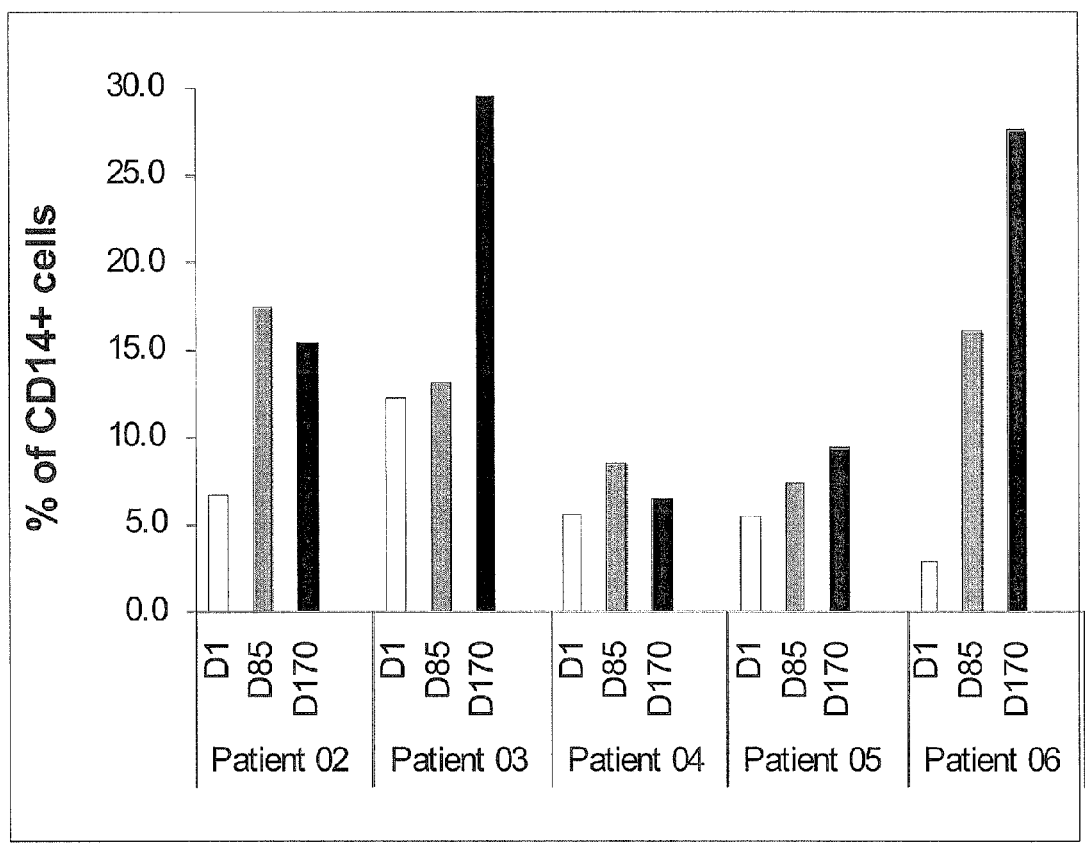
FIG. 1 represents fluorescence-activated cell sorting (FACS) analysis of monocytes (i.e. $CD14^+CD45^+$ cells) in PBMCs from metastatic breast carcinoma patients.

The results are represented in FIG. 1. The results showed a 2.5-fold (at 3 months, Day 85) and a 3.5-fold (at 6 months, Day 170) mean increase of monocyte counts at this low IMP321 dose clinical protocol. In order to confirm the above results, a more direct and probably more accurate approach was carried out, which was to quantify directly ex-vivo the number of monocytes in whole blood (i.e. without prior purification of PBMCs on Ficoll gradient) by first measuring the exact volume of blood to be analyzed with diluted fluorescent beads and then counting the number of $CD14^+$ cells (i.e. monocytes) in the gated $CD45^+$ (leukocytes) cells present in this whole blood volume.

Figure 2:
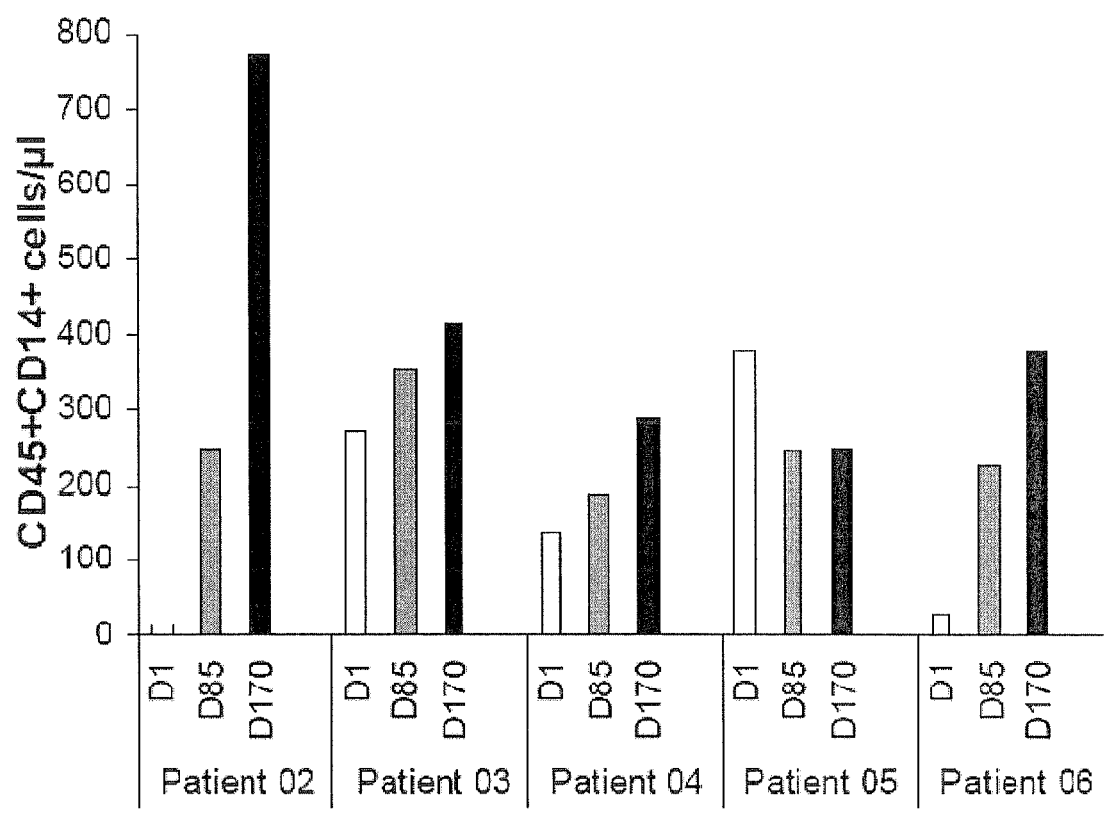
FIG. 2 represents fluorescence-activated cell sorting (FACS) analysis of monocytes (i.e. $CD14^+CD45^+$ cells) in fresh whole blood from metastatic breast carcinoma patients.

The results are represented in FIG. 2. The results showed a 4.4-fold mean increase at Day 170 (2.8-fold at Day 85) when IMP321 was given at low dose (0.25 mg) for a long period of time, 6 months, with 12 injections, showing strong and direct stimulation of the targeted MHC class $II^+$ monocyte-like hematopoietic cells.

Example 2

Monocytes Increase in Metastatic Renal Clear-Cell Carcinoma (MRCC) Patients Using High IMP321 Dose Three MRCC patients each received one subcutaneous IMP321 dose of 6.25 mg every other week, for 12 weeks, separated by 14-day administration-free intervals. Blood samples were collected as described above from each patient, 14 days after the last IMP321 injection (i.e. looking at lasting immunomodulatory effects of the product), at 2 months (Day 57) and 3 months (Day 85), and used immediately. The expansion of $CD14^+$ $CD45^+$ cells was analysed by FACS in fresh blood samples (because monocytes are sensitive to freezing), and compared with the monocyte counts carried out on fresh blood samples collected before IMP321 administration (Day 1).

Figure 3:
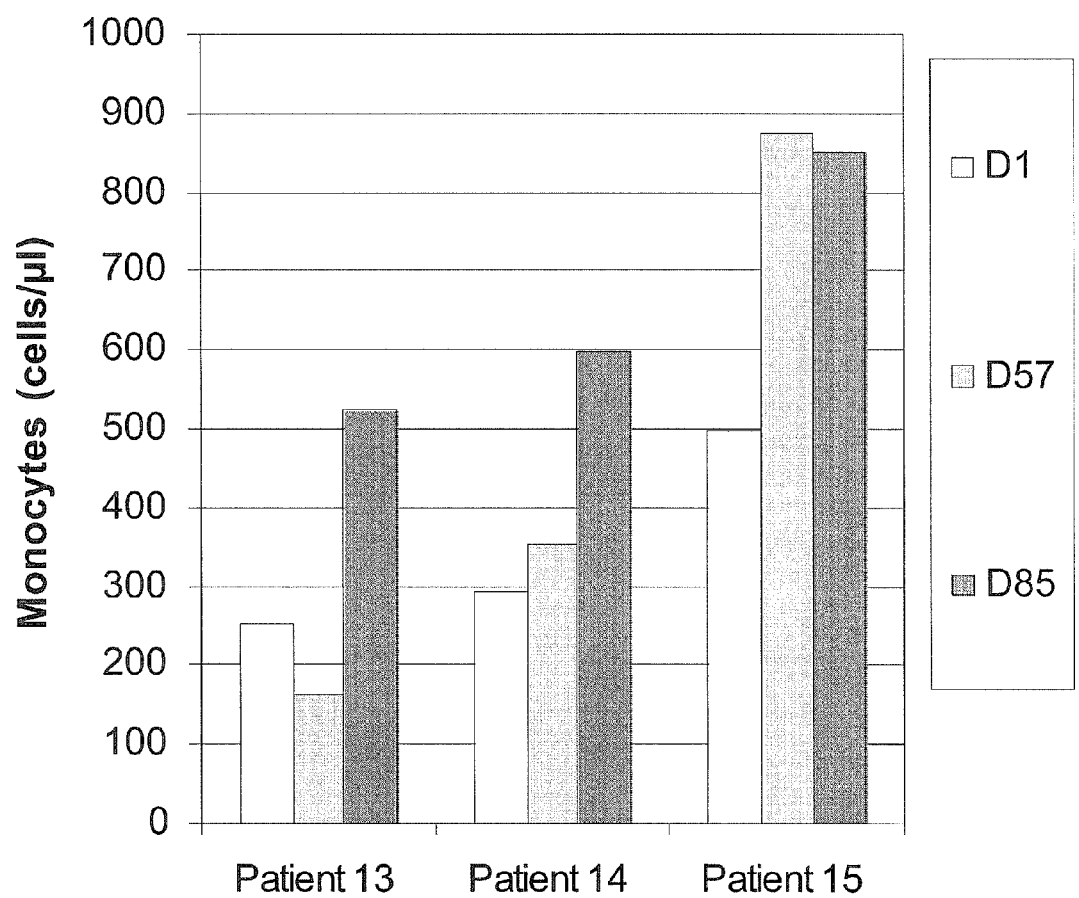
FIG. 3 represents fluorescence-activated cell sorting (FACS) analysis of monocytes (i.e. $CD14^+CD45^+$ cells) in fresh whole blood from metastatic renal cell cancer patients.

The results are represented in FIG. 3. The results showed a 2-fold (at 3 months, Day 85) mean increase of monocyte counts with this high IMP321 dose clinical protocol where patients received only 6 injections.

Example 3

Monocytes Increase in Metastatic Breast Carcinoma Patients Receiving Paclitaxel and IMP321 Doses Patients receiving as a first line chemotherapy for metastatic breast carcinoma 6 cycles of paclitaxel (80 mg/m$^2$ given i.v.) on days 1, 8, and 15 of a 28 day cycle, received 1-30 mg s.c. (sub-cutaneous) IMP321 on days 2 and 16 of each 28-day cycle. Alternatively, IMP321 was administered at days 3 or 17. Accordingly, each patient received a standard 6-month course of weekly paclitaxel with 12 s.c. injections of IMP321, each injection being given one to two days after paclitaxel administration on an every-two-week schedule. The increase in absolute monocyte counts per microliter of fresh blood was analysed by fluorescence-activated cell sorting (FACS), 14 days after the last injection, at 3 months (Day 85) and 6 months (Day 170) compared to day 1.

Figure 4:
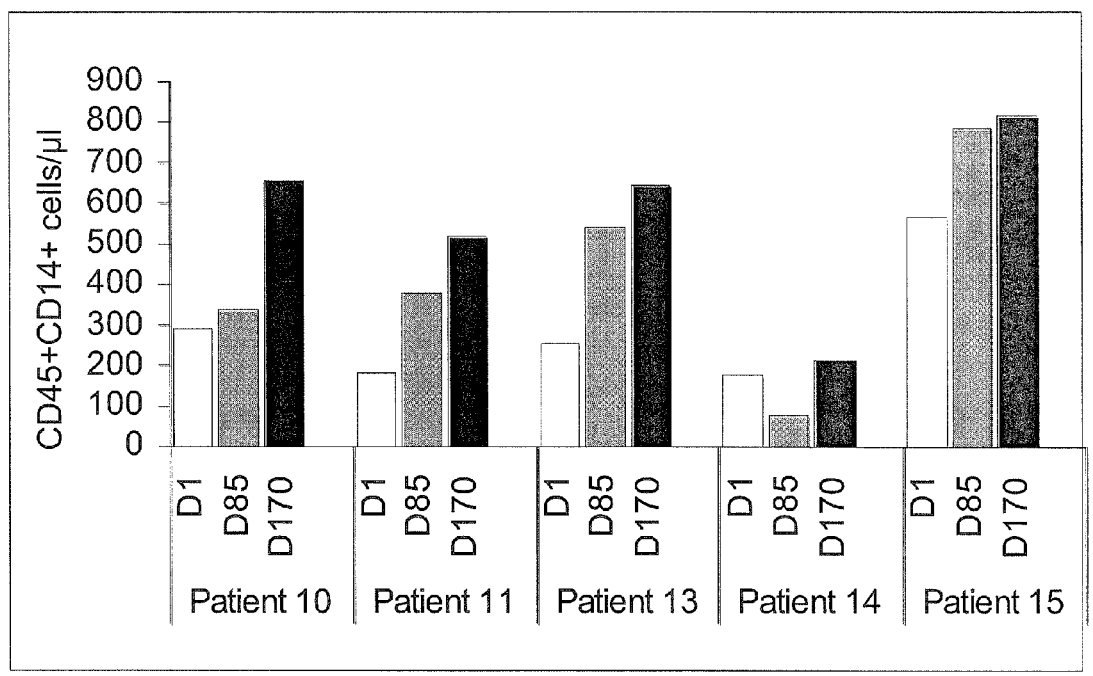
FIG. 4 represents fluorescence-activated cell sorting (FACS) analysis of monocytes (i.e. $CD14^+CD45^+$ cells) in fresh whole blood from metastatic breast carcinoma patients.
Figure 5:
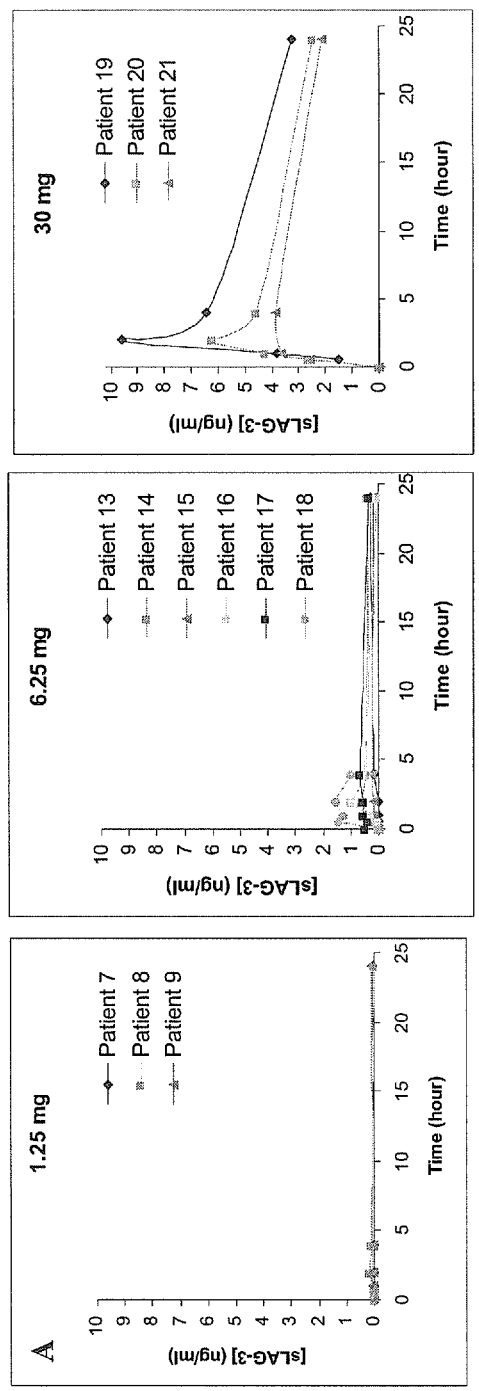
FIG. 5 represents the pharmacokinetic profiles of IMP321 measured by ELISA in the plasma of metastatic renal cell cancer patients.

The results obtained in patients injected with a low dose IMP321 (1.25 mg) are represented in FIG. 4. These data showed that doses of 1.25 mg in most if not all patients (FIG. 4) induce an expansion of the monocyte subset pool in the blood. It is predicted that the optimal dose regimen for IMP321 will be between 6 and 30 mg/injection. These doses have been shown to be safe and give an acceptable systemic exposure based on the results of pharmacokinetics data obtained in metastatic renal cell cancer patients (FIG. 5). A blood concentration of IMP321 superior to 1 ng/ml for at least 24 hours after s.c. injection could be obtained in patients injected by IMP321 doses of more than 6 mg (FIG. 5).

Example 4

Treatment of Advanced Pancreas Cancer Patients Receiving Gemcitabine and IMP321 Doses Patients, receiving as a first line chemotherapy for advanced pancreas cancer (or patients not eligible for surgical removal of the tumor) 6 cycles of standard gemcitabine (1 gm/m² given i.v. over 30 min) on days 1, 8, and 15 of a 28 day cycle, receive in addition 6 to 30 mg s.c. IMP321 on days 2 and 16 of each 28-day cycle. Alternatively, IMP321 is administered at days 3 or 17. Accordingly, each patient receives a standard 6-month course of gemcitabine with 12 s.c. injections of IMP321, each injection being given one to two days after gemcitabine administration on an every-two-week schedule. The number of monocytes is analysed by fluorescence-activated cell sorting (FACS) as in example 1.

Example 5

Induction of Increased Rituximab-mediated ADCC by Low Doses IMP321

PBMCs are first incubated for 40 hours with IL-2 (100 U/ml), with or without IMP321 (at the concentrations 0 µg/m, 0.03 µg/ml or 0.1 µg/ml). PBMCs are then incubated with increasing concentrations of rituximab (0, 0.5 and 5 µg/ml) in the presence of target cells (i.e. human CD20$^+$ Raji B cells). Raji cells were first labeled with CFSE (carboxyfluorescein succinimidyl ester), incubated in medium with rituximab at 0, 0.5 or 5 µg/ml and cocultured with effector cells at an effector-target ratio of 25:1 for 6 hours at 37° C. The cells were then incubated with 7-AAD (7-amino-actinomycin-D) for 15 min on ice and analyzed by flow cytometry to determine the percentage of dead CFSE$^+$ 7-AAD$^+$ Raji target cells (i.e. % of cytotoxicity).

Figure 6:
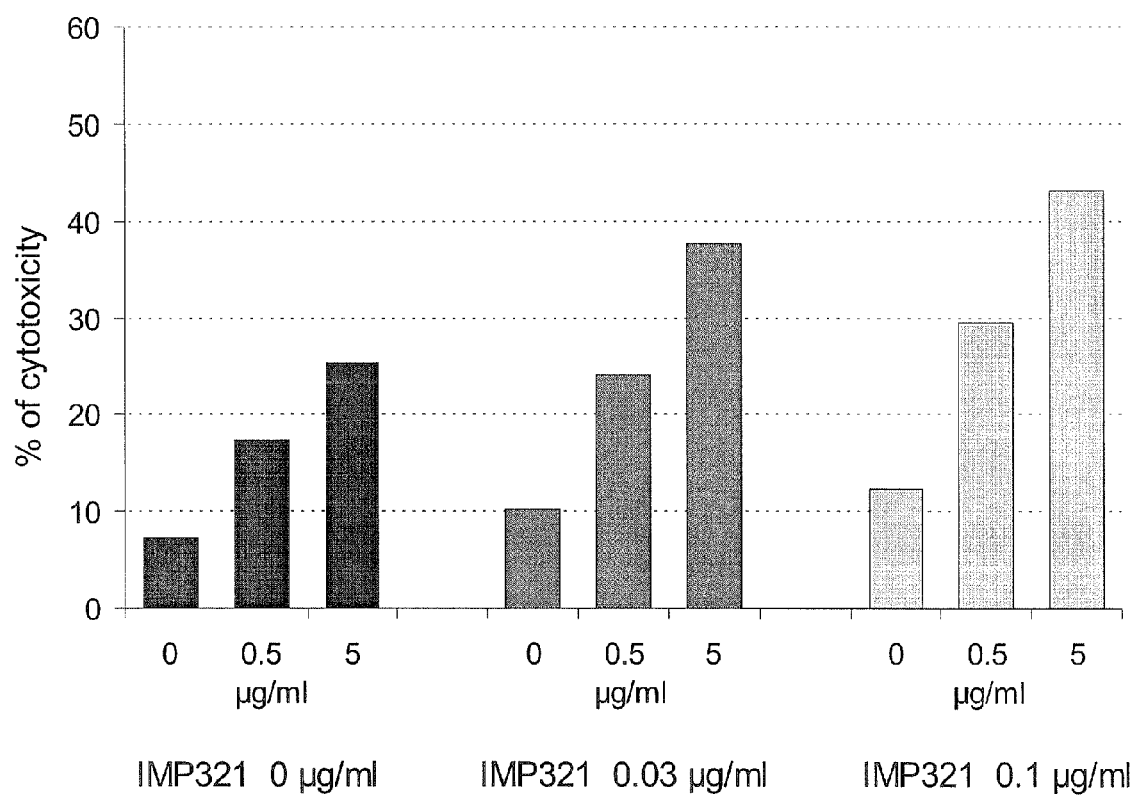
FIG. 6 represents the flow cytometry analysis of PBMC cultured in different conditions with rituximab and/or IMP321.

The results are presented in FIG. 6. Increasing the concentration of rituximab increased the percentage of cytotoxicity, clearly showing a dose-dependent ADCC activity. When 0.03 or 0.1 µg/ml IMP321 is added, the percentage of cytotoxicity greatly increased. For instance, a 30% cytotoxicity is observed with 0.5 µg/ml rituximab in the presence of 0.1 µg/ml IMP321 which is superior to the 25% cytotoxicity value obtained with 5 µg/ml rituximab in the absence of IMP321. Thus, adding 0.1 µg/ml IMP321 potentializes 10-15 fold the activity of rituximab because a superior cytotoxicity is obtained with 10 time less antibody when a low dose IMP321 (0.1 µg/ml) is added. These data show the synergistic effect between rituximab and IMP321.

REFERENCE LIST

[1] TRIEBEL et al., J. Exp. Med., 171: 1393-1405, 1990;
[2] BRIGNONE et al., J. Immune Based Ther Immunotherapies, 5: 5, 2007;
[3] TRIEBEL et al., Trends Immunol., 24: 619-622, 2003;
[4] HUARD et al., Proc. Natl. Acad. Sci. USA, 94: 5744-5749, 1997;
[5] PRIGENT et al., Eur. J. Immunol., 29: 3867-3876, 1999; and
[6] BRIGNONE et al., J. Immunol., 179: 4202-4211, 2007.

The invention claimed is:

1. A method of treating cancer in a human subject in need thereof, which comprises:
   administering to the subject, by systemic administration, an effective plurality of doses of a recombinant human LAG-3 protein or a derivative thereof, wherein the recombinant human LAG-3 protein comprises an extracellular region having the first, second, third and fourth immunoglobulin-like domains of a native human LAG-3 protein and the derivative is selected from the group consisting of:
   i) a fragment of the native human LAG-3 protein comprising the first and second immunoglobulin-like domains of the native human LAG-3 protein;
   ii) a fragment of the native human LAG-3 protein comprising the first, second, third and fourth immunoglobulin-like domains of the native human LAG-3 protein;
   iii) a mutant form of the native human LAG-3 protein, or a fragment thereof that comprises the first and second immunoglobulin-like domains of the native human LAG-3 protein, wherein the mutant comprises a substitution of an amino acid at one or more of the following positions:
      a) position 73 where ARG is substituted with GLU,
      b) position 75 where ARG is substituted with ALA or GLU,
      c) position 76 where ARG is substituted with GLU,
   iv) a variant of the native human LAG-3 protein comprising the first, second, and third immunoglobulin-like domains of the native human LAG-3 protein; and v) a recombinant soluble human LAG-3Ig fusion protein (IMP321) comprising at least the first and second immunoglobulin-like domains of the native human LAG-3 protein fused to human IgG1 Fc;

wherein the recombinant human LAG-3 protein or the derivative thereof is the sole active ingredient in said treatment, and wherein each dose of the recombinant human LAG-3 protein or the derivative thereof is 1-30 mg of the recombinant soluble human LAG-3Ig fusion protein IMP321, or a molar equivalent of 1-30 mg of IMP321;

inducing a systemic increase in the number of monocytes in blood of the subject; and eliciting a systemic monocyte-mediated immune response.

2. The method of claim 1, wherein each dose of the recombinant human LAG-3 protein or derivative thereof is 8-25 mg of the recombinant soluble human LAG-3Ig fusion protein IMP321, or a molar equivalent of 8-25 mg of IMP321.

3. The method of claim 1, wherein one dose of the recombinant LAG-3 protein or derivative thereof is administered every one to several weeks for at least 12 weeks, separated by 13-day±2 days administration-free intervals.

4. The method of claim 1, wherein each dose of the recombinant LAG-3 protein or derivative thereof is formulated so as to allow subcutaneous or intravenous administration.

5. The method of claim 1, wherein the plurality of doses include at least 6 doses.

6. The method of claim 1, wherein the plurality of doses are given on an every-two-week schedule.

7. The method of claim 5, wherein said at least 6 doses are given on an every-two-week schedule.

8. A method of treating cancer in a human subject in need thereof, which comprises:

administering to the subject, by systemic administration, an effective plurality of doses of a recombinant human LAG-3 protein or a derivative thereof, wherein the recombinant human LAG-3 protein comprises an extracellular region having the first, second, third and fourth immunoglobulin-like domains of a native human LAG-3 protein and the derivative is selected from the group consisting of:

i) a fragment of the native human LAG-3 protein comprising the first and second immunoglobulin-like domains of the native human LAG-3 protein;

ii) a fragment of the native human LAG-3 protein comprising the first, second, third and fourth immunoglobulin-like domains of the native human LAG-3 protein;

iii) a mutant form of the native human LAG-3 protein, or a fragment thereof that comprises the first and second immunoglobulin-like domains of the native human LAG-3 protein, wherein the mutant comprises a substitution of an amino acid at one or more of the following positions:

a) position 73 where ARG is substituted with GLU,
b) position 75 where ARG is substituted with ALA or GLU,
c) position 76 where ARG is substituted with GLU, iv) a variant of the native human LAG-3 protein comprising the first, second, and third immunoglobulin-like domains of the native human LAG-3 protein; and v) a recombinant soluble human LAG-3Ig fusion protein (IMP321) comprising at least the first and second immunoglobulin-like domains of the native human LAG-3 protein fused to human IgG1 Fc;

wherein the subject is treated in the absence of any additional antigen, and wherein each dose of the recombinant human LAG-3 protein or the derivative thereof is 1-30 mg of the recombinant soluble human LAG-3Ig fusion protein IMP321, or a molar equivalent of 1-30 mg of IMP321;

inducing a systemic increase in the number of monocytes in blood of the subject; and eliciting a systemic monocyte-mediated immune response.

9. The method of claim 1, wherein each dose of the recombinant LAG-3 protein or derivative thereof is 6-30 mg of the recombinant soluble human LAG-3Ig fusion protein IMP321, or a molar equivalent of 6-30 mg of IMP321.

* * * * *